United States Patent [19]

Tsuchiya et al.

[11] 4,230,886

[45] * Oct. 28, 1980

[54] METHOD OF OBTAINING DRIED TEREPHTHALIC ACID

[75] Inventors: Fujio Tsuchiya; Kenzo Yamamoto; Katsunobu Yamaguchi; Akio Okagami, all of Yokohama, Japan

[73] Assignees: JGC Corporation, Tokyo; Orient Kagaku Kogyo K.K., Osaka, both of Japan

[*] Notice: The portion of the term of this patent subsequent to Aug. 26, 1997, has been disclaimed.

[21] Appl. No.: 46,824

[22] Filed: Jun. 8, 1979

[51] Int. Cl.$^3$ ............................................. C07C 51/42
[52] U.S. Cl. .................................................. 562/486
[58] Field of Search ......................................... 562/486

[56] References Cited

U.S. PATENT DOCUMENTS 3,119,860  1/1964  Kalfadelis et al. ................... 562/486

Primary Examiner—A. Siegel
Attorney, Agent, or Firm—Armstrong, Nikaido, Marmelstein & Kubovcik

[57] ABSTRACT

Terephthalic acid produced by oxidizing paraxylene can be obtained in the form of dried powder from the slurry containing terephthalic acid and acetic acid and/or water by using combination of a tubular type heater having at least one heating tube and a separation chamber in which the heating tube(s) open(s) at one end(s) thereof.

Critical slurry concentrations for smooth operation are given.

9 Claims, 3 Drawing Figures

METHOD OF OBTAINING DRIED TEREPHTHALIC ACID

BACKGROUND OF THE INVENTION

1. Field of the Invention

The present invention relates to a method of obtaining dried terephthalic acid by removing acetic acid and/or water from a slurry containing terephthalic acid, and acetic acid and/or water.

2. State of the Art

Industrial production of terephthalic acid generally employs a process of oxidizing paraxylene, the raw material, in the presence of a salt or salts of heavy metal(s) such as Co or Co+Mn as a catalyst, with molecular oxygen, in liquid medium of lower aliphatic acid, usually acetic acid.

There are a few types of this process using different reaction conditions: some of them provide, after the oxidation step, purification step by hydrogenation in water medium to prepare terephthalic acid of a desired purity; and the others offer, in case where high purity is not required, produced terephthalic acid without purification step.

Anyway, in industrial production of terephthalic acid, it is essential to provide a step of recovering terephthalic acid as a dry powdery material by separating it from acetic acid and/or water used as solvent.

Heretofore, there has been employed a manner of drying terephthalic acid, after draining off in centrifugal separator, to heat and dry it with steam in a rotary drier in the stream of non-condensing gas such as nitrogen. In this manner, it is possible to reduce residual liquid in the terephthalic acid after the drying to about 0.1% by weight.

However, rate of drying in this manner is low because the rate depends on vapor pressure of acetic acid and/or water at the heating temperature. Therefore, there are many problems in the drying: long staying period in the dryer, which requires a large apparatus, decreased heat transfer effect due to adhesion of terephthalic acid on wall of tubes in which heating medium (steam) passes, and resulting troublesome maintenance. Moreover, the drying requires system of recycling gas for the drying such as nitrogen, namely, a blower for the recycling and attached apparatus such as scrubber for recovering entrained terephthalic acid and a heat exchanger for heating the dryer gas. Also, as to the operation of the drying system, it is necessary to maintain a constant rate of draining-off in the centrifugal separator in order to keep smooth feeding of the slurry to the rotary dryer with a screw feeder. If residual liquid content varies, terephthalic acid to be fed becomes solid masses in the screw feeder, which prevents transfer and even forces interruption of operation of the dryer system. Further, perfect gas seal in the rotary dryer is difficult to realize and the dryer gas inevitably leaks.

SUMMARY OF THE INVENTION

The present invention has been achieved with a view to solve the above mentioned problems in drying terephthalic acid.

The object of this invention is to provide a novel method of drying terephthalic acid with significantly reduced trouble in operation without using a rotary dryer.

DRAWINGS

DESCRIPTION OF PREFERRED EMBODIMENTS

The method of obtaining dried terephthalic acid according to the present invention by removing acetic acid and/or water from slurry containing terephthalic acid and acetic acid and/or water is characterized by feeding the slurry to a tubular heater having at least one heating tube which opens at one end in a separation chamber to change the slurry to a solid-gas mixture in the heating tube, discharging the mixture into the separation chamber to separate the solid component and the gas component, thus obtaining terephthalic acid in the form of dried powder; and terephthalic acid content in the slurry being less than the value "C" defined by the formula:

$$C = (2.5\theta^{0.4} + 66)\alpha + (3.2\theta^{0.35} + 74)(1 - \alpha)$$

wherein C is expressed as % by weight, $\theta$ is temperature (°C.) of the heating tube, $\alpha$ is molar ratio of water in the slurry medium and $(1 - \alpha)$ is molar ratio of acetic acid in the slurry medium.

Because it has been anticipated that plugging or blocking up would necessarily occur when a slurry of a high concentration is fed into a heating tube to evaporate the medium, the above mentioned discovery itself is surprising.

The present invention will now be illustrated with reference to the attached drawings.

Figure 1:
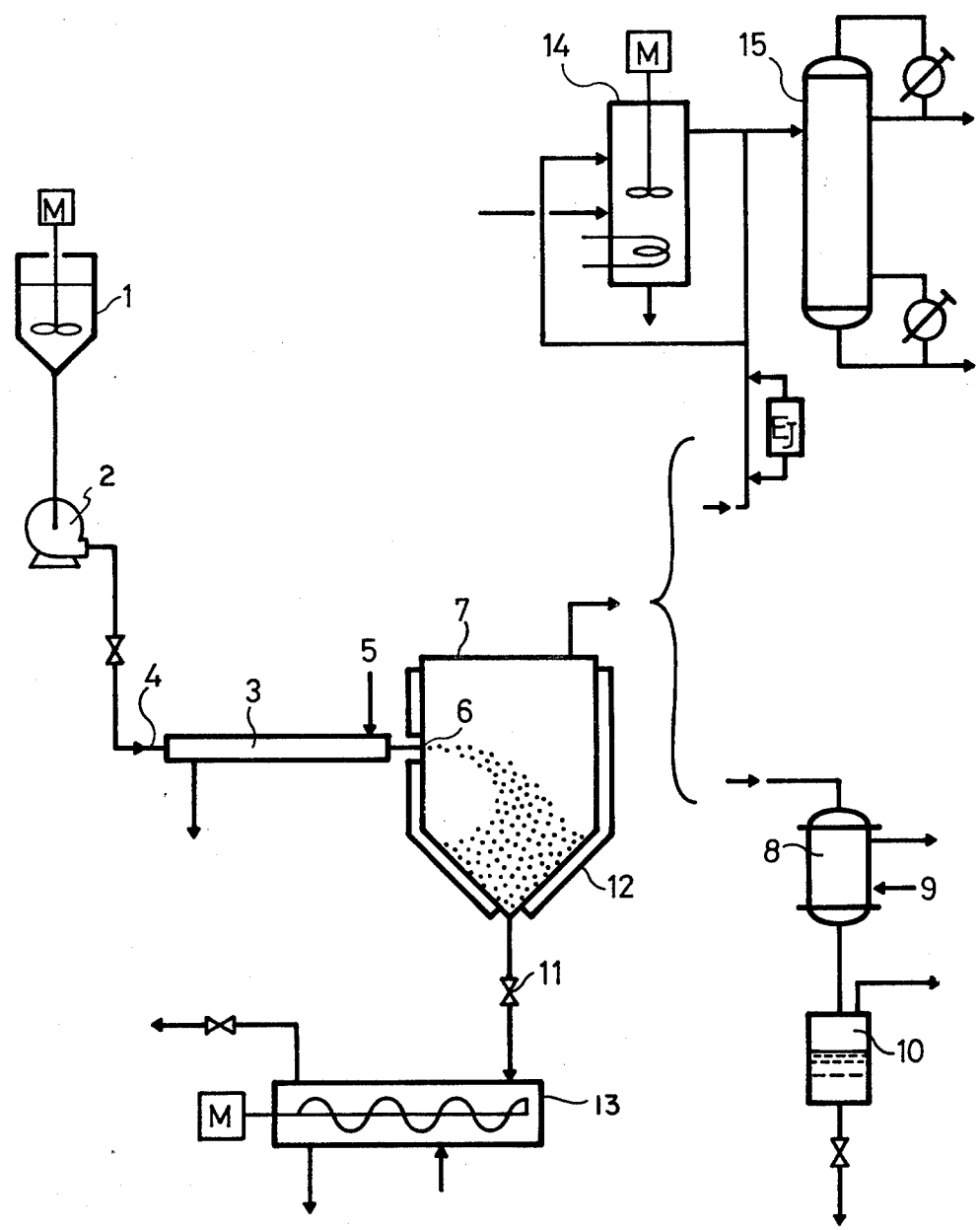
FIG. 1 is a flow chart of apparatus for practicing the method of obtaining dried terephthalic acid of the present invention.

In FIG. 1, slurry from slurry tank 1 is fed by slurry pump 2 into heating tube 3 of a tubular type heater. The slurry fed is heated in the tube with a heating means such as steam (in case of heating above 100° C.) or hot water (in case of heating below 100° C.), or some other heating medium or with electric heating. As the slurry proceeds in the heating tube, acetic acid and/or water evaporate to form a vigorously fluidizing mixture consisting of solid-gas two phases. The outlet end 6 of the heating tube 3 opens in the separation chamber 7, from which end the mixture is discharged, and the solid and the gas separate there.

The gas phase enters in condensor 8 is cooled by cooling water 9 to condense, and the condensate is received in receiver tank 10.

Alternatively, the gas phase is, as it is, introduced into an acetic acid recovery means to separate the acid from water. In the case that the gas component obtained in the separation chamber consists of acetic acid containing water of a certain concentration and that the recovered acetic acid is to be recycled to reactor of paraxylene oxidation, the gas component is, because it is necessary to reduce water content in the acetic acid, passed to acetic acid recovery column 15 so as to recover acetic acid therein. In such a case, the gas component may be passed to the column by way of an acetic acid evaporator 14 which is equipped in the terephthalic acid producing plant for removal of impurity in the reaction mother liquor. Even if the gas component is acetic acid containing water to some extent, the gas may be cooled to condense for recycling and reuse in a step other than the oxidation reaction, such as washing of precipitated terephthalic acid. If the gas component obtained is acetic acid of a high purity, it is advisable to condense the acid and reuse. On the other hand, if the gas mainly consists of water, it should be condensed and passed to a water treatment step.

The solid phase, namely terephthalic acid, accumulates in the separation chamber 7 in the form of dry powder or easily crushable masses, which is taken out continuously or batchwise through valve 11 at the bottom of the chamber 7. The separation chamber 7 is warmed by means of a jacket 12 so that the gas phase may not condense in the chamber.

The system of terephthalic acid and acetic acid and/or water, as far as it contains up to 70% by weight of solid component, can be treated as a slurry in conventional way of conveying such as a slurry pump. Around 75% is the limit allowing treatment as a slurry, and the system of 80% solid loses mobility, and hence it should be referred to as a wet solid mass rather than slurry. According to the present invention, however, system of such a high content as 80 to 90% solid, or even more, can be treated. In this specification, the system, as far as it can be dried in accordance with this method, is referred to as "slurry".

Transfer of a slurry of high concentration which is difficult to be pumped by a slurry pump can be realized by pushing it with pressure gas such as nitrogen or steam into the heating tube.

In the evaporation using the combination of the heating tube and the separation chamber, if the slurry to be treated contains a low content of terephthalic acid, the amount of slurry medium, and consequently, the amount of the gas generated by the evaporation of the medium is relateively large in comparison with the amount of solid terephthalic acid, and therefore, has sufficient effect to fluidize and carry away powdery terephthalic acid. So, it will be readily understood that, in this case, a stable operation without plugging the heating tube can be continued. However, larger amount of medium to be evaporated requires larger amount of heat to be transferred through the heating tube. Thus, it is apparent that the working capacity of the apparatus remains small. This is of course disadvantageous for operation economy. From this point of view, the slurry to be treated by the present method should contain 50% by weight or more of terephthalic acid.

Also, it will be understood that, when the slurry contains higher percentage of terephthalic acid, contrary to the above case, pushing force of the medium and the gas therefrom is weak, and therefore, plugging may occur. As a conclusion, it is preferable for industrial practice to treat a slurry of the highest concentration as far as there is little risk of plugging because of the best utilization of the apparatus and energy consumption.

To add explanation on the above mentioned formula, because the composition of the slurry medium ($\alpha$ and $1-\alpha$) is a given condition depending on the object of the treatment, if the temperature of the heating tube is set at a certain degree, the slurry to be fed should have concentration less than the above noted critical concentration calculated on the basis of the temperature. Alternatively, if it is necessary to treat a slurry having a certain medium composition and a certain slurry concentration, the temperature of the heating tube should be higher than the degree which satisfies the above mentioned equation.

Figure 2:
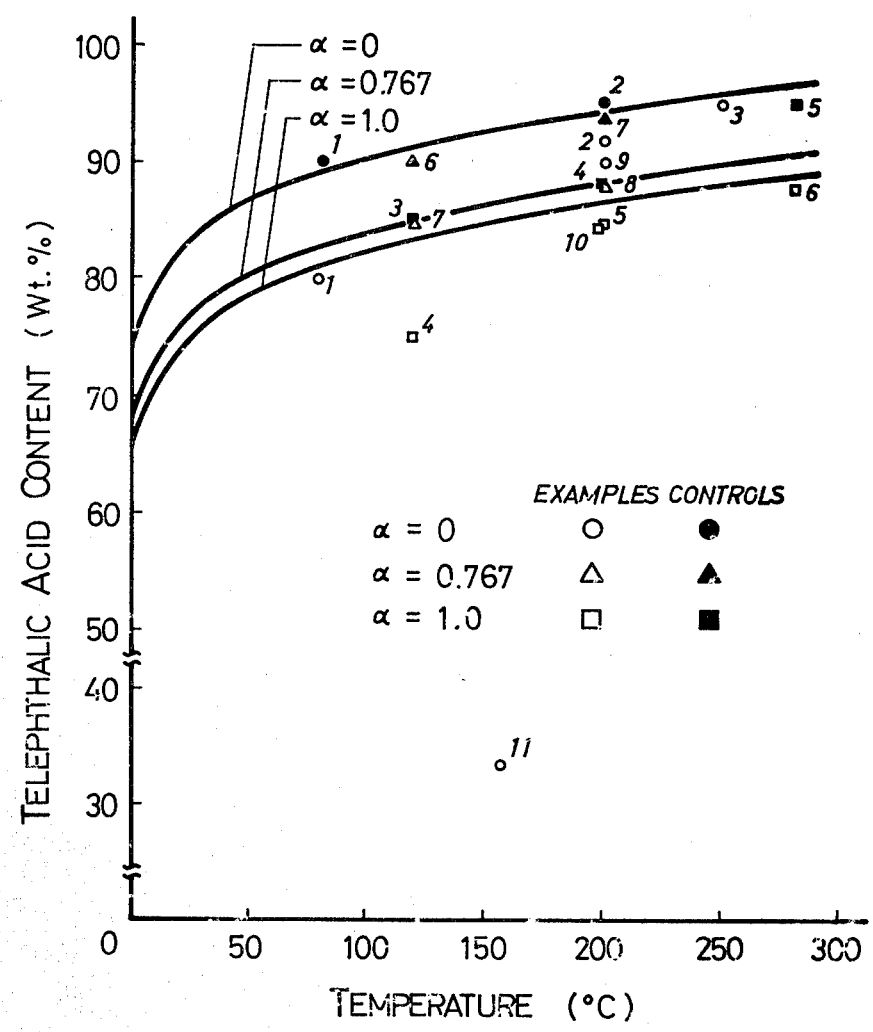
FIG. 2 shows relationship between temperatures and critical slurry concentrations defined in the present invention.

FIG. 2 shows the above relationship. The three curves indicates the critical slurry concentrations at various temperatures of the systems of $\alpha=0$ (the medium consists of only acetic acid), $\alpha=0.767$ (acetic acid/water=1/3.3) and $\alpha=1.0$ (water only). When the treatment of the slurry is conducted with the conditions in the regions below these curves, the treatment can be continued without plugging of the heating tube.

The pressure in the separation chamber can vary in a wide range. Operation under a pressure lower than atmospheric pressure or vacuum condition is suitable for the case where it is intended to cool and condense the volatile component.

On the other hand, acetic acid separated from terephthalic acid is, in many cases, recovered to reuse as the medium for paraxylene-oxidation step. In case where the operation is conducted with a reduced pressure of the separation chamber, the separated acetic acid or acetic acid containing water passes to an acetic acid evaporator or an acetic acid distillation column in liquid state as the result of cooling and condensation, and heated again to become gaseous state. This cooling and reheating is disadvantageous from view points of energy consumption, and it is advantageous to introduce acetic acid to the recovery means in the gaseous state. If the pressure in the separation chamber is lower than that of the acetic acid recovery column, it is recommended to push in the gas component containing acetic acid by using an ejector. As the driving gas for the ejector, acetic acid vapor from reboiler of the acetic acid recovery column can be used.

In order to pass acetic acid in the state of vapor, it is recommended to operate with a higher pressure, e.g. normal to a few kgms per cm$^2$, of the separation chamber. There is no upper limit of the pressure unless the gas component does not liquify. Practically, however, it is advisable to use normal pressure to 6 kg/cm$^2$ abs or so because of easiness in construction of apparatus and operation. Too high a pressure gives no particular merit. The acetic acid recovery means into which the gas component is introduced is usually operated under a normal pressure.

When the pressure in the separation chamber is high, the temperature of the heating tube must be accordingly high. The suitable temperature of the heating tube also depends on the system of the slurry medium.

Figure 3:
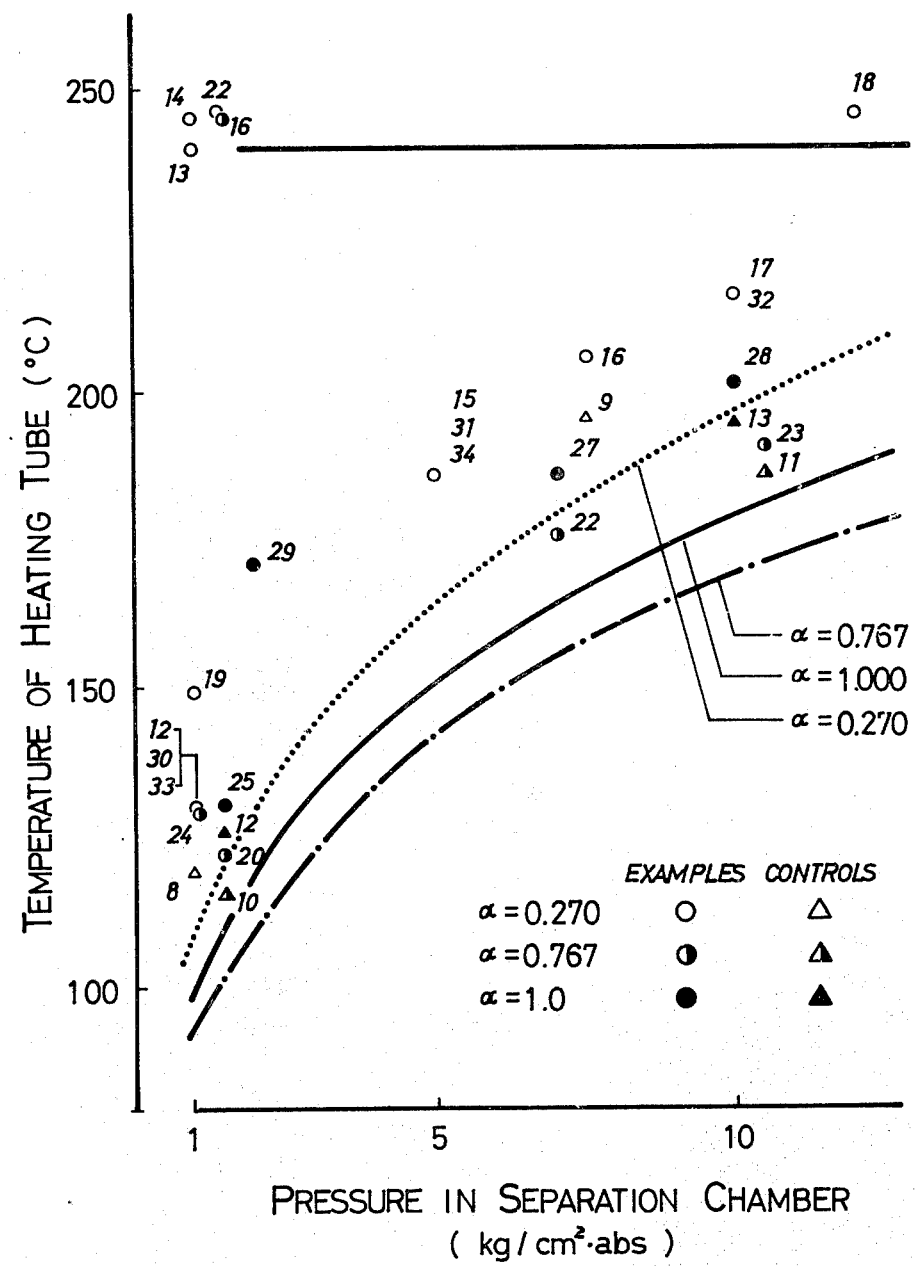
FIG. 3 shows gas-liquid equilibrium curves of acetic acid-water system, which gives relationship between pressures in the separation chamber and temperatures of the heating tube to be chosen in case of practicing the method under a higher pressure.

FIG. 3 shows gas-liquid equilibrium curves of the system in which acetic acid: water is 0:100, 50:50 and 90:10 by weight or $\alpha=1.000$, $\alpha=0.767$, and $\alpha=0.270$ by molar ratio of water. The regions below these curves are condensing regions in which the slurry medium is in liquid phase. Needless to say, it is necessary to use conditions in the regions above these curves. Perfect separation will be performed at a temperature 20° C. or more higher than the equilibrium temperature.

It is experienced, however, that too elevated temperature often disgrades quality of the product, terephthalic acid, by, for example, changing color. In order to avoid the possible disgrading, experimental results gave a conclusion that maximum temperature of the heating tube must be up to 240° C.

If it is intended to reduce residual liquid in the product terephthalic acid to the extreme, it is recommended to receive terephthalic acid in powder form or easily crushable mass, as shown in FIG. 1, through a valve 11 in a receiver 13, and to keep the receiver under a reduced pressure lower than the pressure in the separation chamber, or to keep under a vacuum by connecting to a vacuum device. It is effective to agitate the product in the receiver with an agitator (e.g., by using a ribbon blender). Also, it is useful to stream a dry inert gas such as nitrogen, preferably after being heated to some extent, through the receiver. The gas streaming is preferably conducted with the reduced pressure operation.

Thus, dried terephthalic acid can be obtained in accordance with the present invention without any trouble related to the conventional manner which uses a rotary dryer. Because a slurry of high concentrations can be treated the drying of this method is performed with a very high efficiency and low energy consumption. As far as the procedure satisfies the conditions defined by the above mentioned formula, no plugging of the heating tube occurs and the stable operation can be continued.

EXAMPLE 1

Terephthalic acid slurry was dried by using apparatus as shown in FIG. 1. The separation chamber has a glass window through which ejection of terephthalic acid powder from open end of the heating tube can be observed. In the event of plugging, it can be promptly recognized due to termination of the powder ejection.

A slurry which contained 80% by weight of solid and medium of which consisted of acetic acid only was fed to the heating tube. Feeding of the slurry was smoothly performed by aspiration from the separation chamber which was kept at 120 mm Hg. The temperature of the heating tube was kept at 80° C. with hot water.

The operation continued without any plugging of the tube. After 30 minutes running, terephthalic acid accumulated at the bottom of the separation chamber was taken out. The product was subjected to determination of residual liquid content by being heated in an electric oven under nitrogen atmospher for 2 hours to give the observed value, 650 ppm.

CONTROL 1

The same procedure as Example 1 was repeated with higher terephthalic acid slurry content, 90%.

About 2 minutes after beginning of the operation, plugging occurred. Then, the slurry was pushed with compressed gas of 5 kg/cm² abs, but the plugging was not dissolved.

In case where the slurry tank was pressurized to 5 kg/cm² abs from the beginning plugging was also observed in a few minutes.

Inspection of the heating tube revealed that inside of the tube was entirely packed with terephthalic acid in wet state and powder.

EXAMPLES 2 to 10

Drying operation of terephthalic acid was repeated with varied slurry contents, medium compositions and temperatures of the heating tube, which satisfy the conditions defined by the above mentioned formula. Extent of vacuum in the separation chamber was also varied.

In all the cases operation continued long to give highly dried terephthalic acid powder.

CONTROLS 2 to 7

Drying operation was repeated with varied slurry contents, medium compositions and temperatures of the heating tube, which dissatisfy the conditions inherent in the present method.

Plugging of the heating tube occurred after a short time of running, and was unable to be recovered.

The operation conditions and results of the above Examples and Control Examples are given in Table I and Table II respectively.

Also, the temperatures and slurry contents of the Examples and Control Examples are plotted in FIG. 2 with reference numbers.

TABLE I

| | | Examples | | | |
|---|---|---|---|---|---|
| Run | Slurry Medium | Slurry Concn. (Wt. %) | Temp. of Heating (°C.) | Press. in Sep. Chamb. (mmHg) | Continuous Operation | Residual Liquid (ppm) |
| 1 | $\alpha = 0$ | 80 | 80 | 120 | yes | 650 |
| 2 | " | 92 | 200 | 300 | " | 710 |
| 3 | " | 95 | 250 | 300 | " | 750 |
| 4 | $\alpha = 1.0$ | 75 | 120 | 300 | " | 350 |
| 5 | " | 85 | 200 | 300 | " | 420 |
| 6 | " | 88 | 280 | 300 | " | 480 |
| 7 | $\alpha = 0.767$ | 85 | 120 | 300 | " | 470 |
| 8 | " | 88 | 200 | 300 | " | 460 |
| 9 | $\alpha = 0$ | 90 | 200 | 600 | " | 720 |
| 10 | $\alpha = 1.0$ | 85 | 200 | 600 | " | 650 |
| 11 | $\alpha = 0$ | 33 | 158 | 300 | " | 560 |

TABLE II

| | | Controls | | | |
|---|---|---|---|---|---|
| Run | Slurry Medium | Slurry Concn. (Wt. %) | Temp. of Heating Tube (°C.) | Press. in Sep. Chamb. (mmHg) | Continuous Operation |
| 1 | $\alpha = 0$ | 90 | 80 | 120 | No (plugging 2 min. after) |
| 2 | " | 95 | 200 | 300 | No (plugging 3 min. after) |
| 3 | $\alpha = 1.0$ | 85 | 120 | 300 | No |
| 4 | " | 88 | 200 | 300 | No |
| 5 | " | 95 | 280 | 300 | No (plugging 5-6 min. after) |
| 6 | $\alpha = 0.767$ | 90 | 120 | 300 | No |
| 7 | " | 94 | 200 | 300 | No |

EXAMPLE 12

In the same apparatus as used in Example 1 to which a receiver of the solid product is attached, there was fed to the heating tube a slurry containing 60% by weight of solid and medium of which consists of 90% by weight of acetic acid and 10% by weight of water ($\alpha=0.270$). The heating tube was heated with steam to 130° C. Pressure in the separation chamber was 1 kg/cm² abs or normal pressure.

The above conditions resulted in a continuation of the operation without plugging of the heating tube. After 10 minutes of running, the valve at the bottom of the separatinn chamber was shut, and terephthalic acid was taken out from the receiver.

Residual liquid was determined by the above mentioned method to be 740 ppm.

EXAMPLES 13 TO 29 AND CONTROLS 8 to 13

The procedure of Example 12 were repeated with different slurry media, slurry concentrations, temperatures of the heating tube and pressures in the separation chamber.

The results of Examples 13 to 29 are shown in Table III, and the results of Controls 8 to 13 in Table IV.

EXAMPLES 31 and 32

Example 30 was repeated with different temperatures of the heating tube and pressures in the separation chamber.

EXAMPLE 33

Terephthalic acid was separated from volatile matters under the same conditions as Example 12. After 10 minutes running, the valve at the bottom of the separation chamber was shut, and nitrogen gas which was heated to some extent was introduced into the receiver at the rate of 100 l/hr for 5 minutes.

TABLE III

Examples

| Run | Slurry Medium | Slurry Concn. (Wt. %) | Temp. of Heating Tube (°C.) | Press. in Sep. Chamb. (kg/cm²abs) | Continuous Opern. | Product Acid Resd. Liq. (ppm) | Appearance |
|---|---|---|---|---|---|---|---|
| 12 | α = 0.270 | 60 | 130 | 1 | yes | 740 | good |
| 13 | " | 60 | 240 | 1 | " | 510 | " |
| 14 | " | 60 | 245 | 1 | " | 510 | yellowish |
| 15 | " | 60 | 185 | 5 | " | 930 | good |
| 16 | " | 60 | 205 | 7.5 | " | 960 | " |
| 17 | " | 60 | 215 | 10 | " | 1230 | " |
| 18 | " | 60 | 245 | 12 | " | 1250 | yellowish |
| 19 | " | 90 | 150 | 1 | " | 710 | good |
| 20 | α = 0.767 | 60 | 122 | 1.5 | " | 710 | " |
| 21 | " | 60 | 245 | 1.5 | " | 480 | yellowish |
| 22 | " | 60 | 175 | 7 | " | 860 | good |
| 23 | " | 60 | 190 | 10. | " | 1100 | " |
| 24 | " | 85 | 130 | 1 | " | 770 | " |
| 25 | α = 1.000 | 60 | 130 | 1.5 | " | 620 | " |
| 26 | " | 60 | 245 | 1.5 | " | 450 | yellowish |
| 27 | " | 60 | 185 | 7 | " | 810 | good |
| 28 | " | 60 | 200 | 10 | " | 780 | " |
| 29 | " | 85 | 170 | 2 | " | 580 | " |

TABLE IV

Controls

| Run | Slurry Medium | Slurry Concn. (Wt. %) | Temp. of Heating Tube (°C.) | Press. in Sep. Chamb. (kg/cm²abs) | Continuous Opern. | Product Acid Resd. Liqd. (ppm) | Appearance |
|---|---|---|---|---|---|---|---|
| 8 | = 0.270 | 60 | 120 | 1 | yes | | |
| 9 | " | 60 | 195 | 7.5 | " | not determined | contained |
| 10 | = 0.767 | 60 | 115 | 1.5 | " | mined | wet |
| 11 | " | 60 | 185 | 10.5 | " | | |
| 12 | = 1.000 | 60 | 125 | 1.5 | " | (large amount) | masses |
| 13 | " | 60 | 195 | 10 | " | | |

EXAMPLE 30

A ribbon blender was used as the receiver of terephthalic acid, and the solid-gas separation was performed under the same conditions as Example 12.

After 10 minutes running, valve 11 was shut, and the pressure in the receiver was decreased to 0.1 kg/cm² abs. Then, nitrogen gas was introduced in the receiver under agitation. Terephthalic acid was taken out after increasing the pressure in the receiver to atmospheric. Residual liquid was determined as low as 350 ppm.

EXAMPLE 34

Example 31 was repeated except that the pressure in the ribbon blender was 1.5 kg/cm² abs. These conditions correspond to modification of Example 4 in which a receiver, though not vacuumed) was used under a pressure lower than that in the separation chamber.

The results of the above Examples 30 to 34 are given in Table V.

Temperature-pressure conditions of Examples 13 through 34 and Controls 8 through 13 are plotted in FIG. 3.

TABLE V

| | | | | | | Product Acid | |
|---|---|---|---|---|---|---|---|
| | | | Examples | | | | |
| Run | Slurry Medium | Slurry Concn. (Wt. %) | Temp. of Heating Tube (°C.) | Press. in Sep. Chamb. (kg/cm²abs) | Press. in Receiver (kg/cm²abs) | Resd. Liqd. (ppm) | Appearance |
| 30 | = 0.270 | 60 | 130 | 1 | 0.1 | 350 | good |
| 31 | " | 60 | 185 | 5 | 0.1 | 320 | " |
| 32 | " | 60 | 215 | 10 | 0.1 | 370 | " |
| 33 | " | 60 | 130 | 1 | 0.1 | 380 | " |
| 34 | " | 60 | 185 | 5 | 1.5 | 780 | " |

We claim:

1. A method of obtaining dried terephthalic acid by removing acetic acid and/or water from a slurry containing terephthalic acid and acetic acid and/or water, characterized by feeding the slurry to a tubular type heater having at least one heating tube which opens at one end in a separation chamber to change the slurry to a solid-gas mixture in the heating tube, discharging the mixture into the separation chamber to separate the solid component and the gas component, thus obtaining terephthalic acid in the form of dried powder; and terephthalic acid content in the slurry being less than the value "C" defined by the formula:

$$C=(2.5\theta^{0.4}+66)\alpha+(3.2\theta^{0.35}+74)(1-\alpha)$$

wherein C is expressed as % by weight, $\theta$ is temperature (°C.) of the heating tube, $\theta$ is molar ratio of water in the slurry medium and $(1-\alpha)$ is molar ratio of acetic acid in the slurry medium.

2. A method according to claim 1, wherein the operation is carried out with a pressure in the separation chamber lower than the atmospheric pressure.

3. A method according to claim 2, which involves further step of passing the gas component separated in the separation chamber to an acetic acid recovery column, optionally by way of an acetic acid evaporator, by means of an ejector to recover acetic acid.

4. A method according to claim 1, wherein the operation is carried out under the condition that the pressure in the separation chamber is at atmospheric pressure or higher and that the temperature around the open end of the heating tube is at least 20° C. higher than the dew point of the slurry medium under the pressure in the separation chamber.

5. A method according to claim 4, wherein the pressure in the separation chamber is in the range from atmospheric pressure to 6 kg/cm² abs.

6. A method according to claim 4 or 5, which involves further step of passing the gas component separated in the separation chamber to an acetic acid recovery column, optionally by way of an acetic acid evaporator to recover acetic acid.

7. A method according to claim 4, wherein the temperature of the heating tube does not exceed 240° C.

8. A method as in any of claims 4, 5, or 7, wherein terephthalic acid powder is received in a receiver by way of a valve at the bottom of the separation chamber, and wherein the receiver of the separation chamber is subjected to a reduced pressure lower than the pressure in the separation chamber and/or an inert gas is passed through the receiver so as to further dry the terephthalic acid.

9. A method as in claim 6, wherein terephthalic acid powder is received in a receiver by way of a valve at the bottom of the separation chamber, and wherein the receiver separation chamber is subjected to a reduced pressure lower than the pressure in the separation chamber and/or an inert gas is passed through the receiver so as to further dry the terephthalic acid.

* * * * *

UNITED STATES PATENT AND TRADEMARK OFFICE
CERTIFICATE OF CORRECTION

PATENT NO. : 4,230,886
DATED : October 28, 1980
INVENTOR(S) : TSUCHIYA ET AL

It is certified that error appears in the above-identified patent and that said Letters Patent are hereby corrected as shown below:

Claim 1, line 15: "$\theta$ is molar ratio" should read -- $\alpha$ is molar ratio--.

Claim 9, line 4: between "receiver" and "separation chamber" insert --of the--.

Signed and Sealed this

Twenty-eighth Day of April 1981

[SEAL]

Attest:

RENE D. TEGTMEYER

Attesting Officer

Acting Commissioner of Patents and Trademarks